(12) United States Patent
Koo et al.

(10) Patent No.: US 9,395,095 B2
(45) Date of Patent: Jul. 19, 2016

(54) AIR PURIFYING APPARATUS HAVING SHUNTABLE AIR DUCT

(71) Applicant: SEOUL VIOSYS CO., LTD., Ansan-si, Gyeonggi-do (KR)

(72) Inventors: Jong Hyun Koo, Ansan-si (KR); Dae Woong Suh, Ansan-si (KR); Young Hwan Son, Ansan-si (KR); Seong Min Lee, Ansan-si (KR); Jae Seon Yi, Ansan-si (KR); Jung Yeol Park, Ansan-si (KR); Sang Hee Cho, Ansan-si (KR); Ju Won Yoo, Ansan-si (KR); Sung Lim Cho, Ansan-si (KR); Jong Rack Kim, Ansan-si (KR)

(73) Assignee: SEOUL VIOSYS CO., LTD., Ansan-si, Gyeonggi-do (KR)

( * ) Notice: Subject to any disclaimer, the term of this patent is extended or adjusted under 35 U.S.C. 154(b) by 0 days.

(21) Appl. No.: 14/453,337

(22) Filed: Aug. 6, 2014

(65) Prior Publication Data
US 2015/0044101 A1  Feb. 12, 2015

(30) Foreign Application Priority Data
Aug. 9, 2013  (KR) .......................... 10-2013-0095028

(51) Int. Cl.
*F24F 3/16* (2006.01)
*A61L 2/10* (2006.01)
*A61L 9/20* (2006.01)

(52) U.S. Cl.
CPC ................. *F24F 3/1603* (2013.01); *A61L 2/10* (2013.01); *A61L 9/205* (2013.01); *F24F 3/166* (2013.01); *A61L 2202/23* (2013.01); *F24F 2003/1625* (2013.01); *F24F 2003/1667* (2013.01)

(58) Field of Classification Search
CPC ...................................................... F24F 3/1603
USPC ............................................................. 422/121
See application file for complete search history.

(56) References Cited

U.S. PATENT DOCUMENTS

| | | | |
|---|---|---|---|
| 6,787,782 B1 * | 9/2004 | Krosney et al. | 250/436 |
| 8,834,805 B2 * | 9/2014 | Owen et al. | 422/186.3 |
| 2009/0236439 A1 * | 9/2009 | Pankhurst | A61L 9/02 239/57 |

FOREIGN PATENT DOCUMENTS

| | | | |
|---|---|---|---|
| KR | 1020072347 | * | 11/2007 |
| KR | 10-2009-0051635 A | | 5/2009 |
| KR | 10-2011-0096258 A | | 8/2011 |

OTHER PUBLICATIONS

Mills, Pneumatic conveying design guide, 1990, Warren Spring Laboratory, p. 60.*

* cited by examiner

*Primary Examiner* — Kevin Joyner
*Assistant Examiner* — Holly Mull
(74) *Attorney, Agent, or Firm* — Plumsea Law Group, LLC (57) ABSTRACT

An air purifying apparatus according to an embodiment includes a body having first and second conduits through which a flow of air is generated from an air inlet to an air outlet, an ultraviolet light emitting diode part and a first filter part disposed within the first conduit, and a second filter part disposed within the second conduit.

20 Claims, 7 Drawing Sheets

AIR PURIFYING APPARATUS HAVING SHUNTABLE AIR DUCT

CROSS-REFERENCES TO RELATED APPLICATIONS

The present application claims priority under 35 U.S.C 119(a) to Korean Application No. 10-2013-0095028, filed on Aug. 9, 2013, in the Korean Intellectual Property Office, which is incorporated herein by reference in its entirety.

BACKGROUND

Exemplary embodiments of the present disclosure relate to an air purifying apparatus, and more particularly, to an air purifying apparatus having a shuntable air duct.

In recent years, air quality has becomes rapidly worse in nations such as Korea. For example, air contaminants generated as the result of rapid industrialization of China are carried into Korea by yellow dust, and thus the concentration of hazardous heavy metals in air is a significant level of concern in Korea. In addition, indoor air within buildings can be contaminated by contaminants such as fine dust, formaldehyde, and floating bacteria. These contaminants may cause sick building syndromes such as dry nose, eye, and throat, pain in the nose, eye, and throat, sneezes, nasal stuffiness, and fatigue.

This environment increases the demand for air purifying apparatus capable of purifying contaminated air. Most of air purifying apparatus that are commonly used today use various filters such that air is purified by introducing contaminated air and filtering out contamination particles in a physical manner or through adsorption using the filters.

Recently, in order to improve purification performance, the mesh of filters used in air purifying apparatus has increased. That is, the number of holes per unit length in the filter is increased so as to filter or adsorb more fine particles. However, as the mesh of the filter is increased, a differential pressure of air applied to front and rear ends of the filter consequently increases as well. As a result, air volume and air pressure are decreased at the air outlet. Conventionally, in order to increase air volume and air pressure at an air outlet, the approach used is to enlarge the blower fan or to otherwise improve the performance of the blower fan. However, since this method results in an increase in product costs, a measure to complement the approach described above is required.

SUMMARY

This summary is intended to provide an overview of the subject matter of this patent, and is not intended to identify essential elements or key elements of the subject matter, nor is it intended to be used to determine the scope of the claimed embodiments. The proper scope of this patent may be ascertained from the claims set forth below in view of the detailed description below and the drawings.

Embodiments of the present apparatus relate to an air purifying apparatus capable of selectively controlling air volume and air pressure at an air outlet.

In one embodiment, an air purifying apparatus includes a body having first and second conduits through which air flows from an air inlet to an air outlet, an ultraviolet light emitting diode part and a first filter part disposed within the first conduit, and a second filter part disposed within the second conduit.

In this embodiment, the first and second conduits may be disposed so as to be compatible with each other and are selectively openable and closable.

In some embodiments, a filter included in the filter part may have a relatively larger differential pressure between front and rear ends of the filter, compared to a filter included in the second filter part.

In some embodiments, the filter included in the first filter part may have a larger mesh than the filter included in the second filter part.

In some embodiments, the first filter part may include a photocatalytic filter and a collection filter, and the second filter part may include a carbon filter.

In other embodiments, the air purifying apparatus includes a body having an air inlet and an air outlet, an air circulation device to form a flow of air from the air inlet to the air outlet, first and second conduits allowing the flow of air to branch within the body, and first and second filter parts respectively disposed within the first and second conduits.

BRIEF DESCRIPTION OF THE DRAWINGS

The above and other aspects, features and other advantages will be more clearly understood from the following detailed description taken in conjunction with the accompanying drawings, in which.

DESCRIPTION OF SPECIFIC EMBODIMENTS

Hereinafter, embodiments of the present disclosure will be described with reference to accompanying drawings. However, the embodiments are for illustrative purposes only and are not intended to limit the scope of the disclosure. For clarity, the detailed descriptions herein describe certain exemplary embodiments, but the disclosure in this application may be applied to any air purification apparatus comprising certain of the features described herein and recited in the claims. In particular, although the following detailed description describes certain exemplary embodiments of air purification apparatus, it should be understood that other embodiments may have different structures, forms, and configurations. The drawings may not be to scale, and the widths, lengths, and thicknesses shown may be exaggerated for clarity.

Unless stated otherwise, terms such as "first" and "second" in the specification of the present disclosure are used to arbitrarily distinguish between the elements such terms describe. Thus, these terms are not necessarily intended to indicate temporal or other prioritization of such elements. In addition, terms "on," "above," "below," and "adjacent" as used herein refer to a position of one element relative to other elements. As such, an element disposed on, above, or below another element may be directly in contact with the other element or it may include one or more intervening elements. It will be understood that when an element is referred to as being "connected" or "arranged" to another element, it can be directly connected or arranged to the other element or intervening elements may also be present. In contrast, when an element is referred to as being "directly connected" or "directly arranged" to another element, there are no intervening elements present.

Throughout the disclosure, like reference numerals refer to like parts throughout the various figures and embodiments of the present disclosure.

Figure 1A:
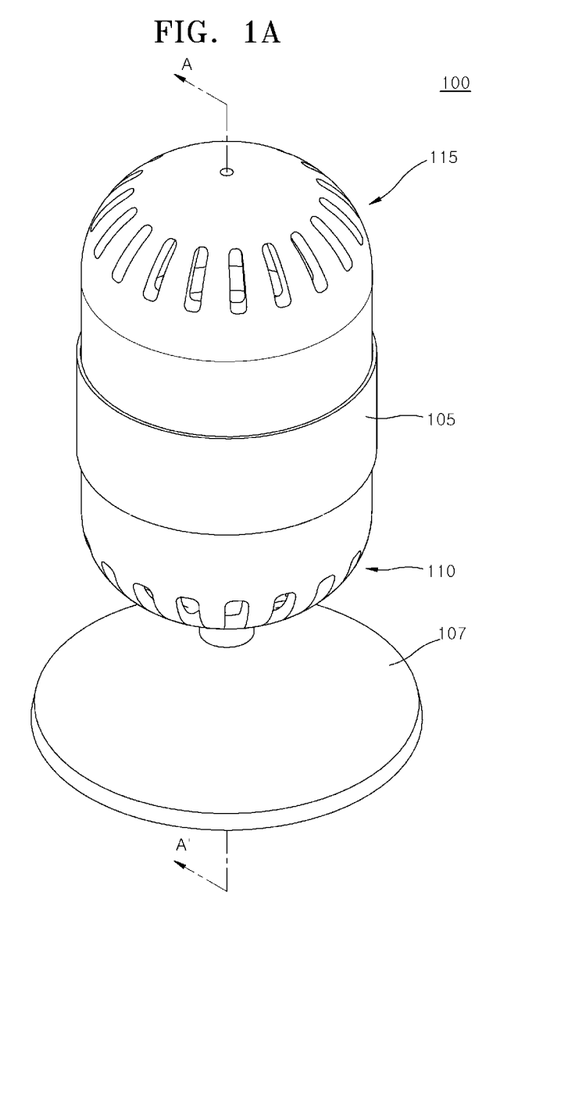
FIG. 1A is a view schematically illustrating an air purifying apparatus according to an embodiment of the air purifying apparatus.

FIG. 1A is a view schematically illustrating an air purifying apparatus according to an embodiment of the present disclosure.

Figure 1B:
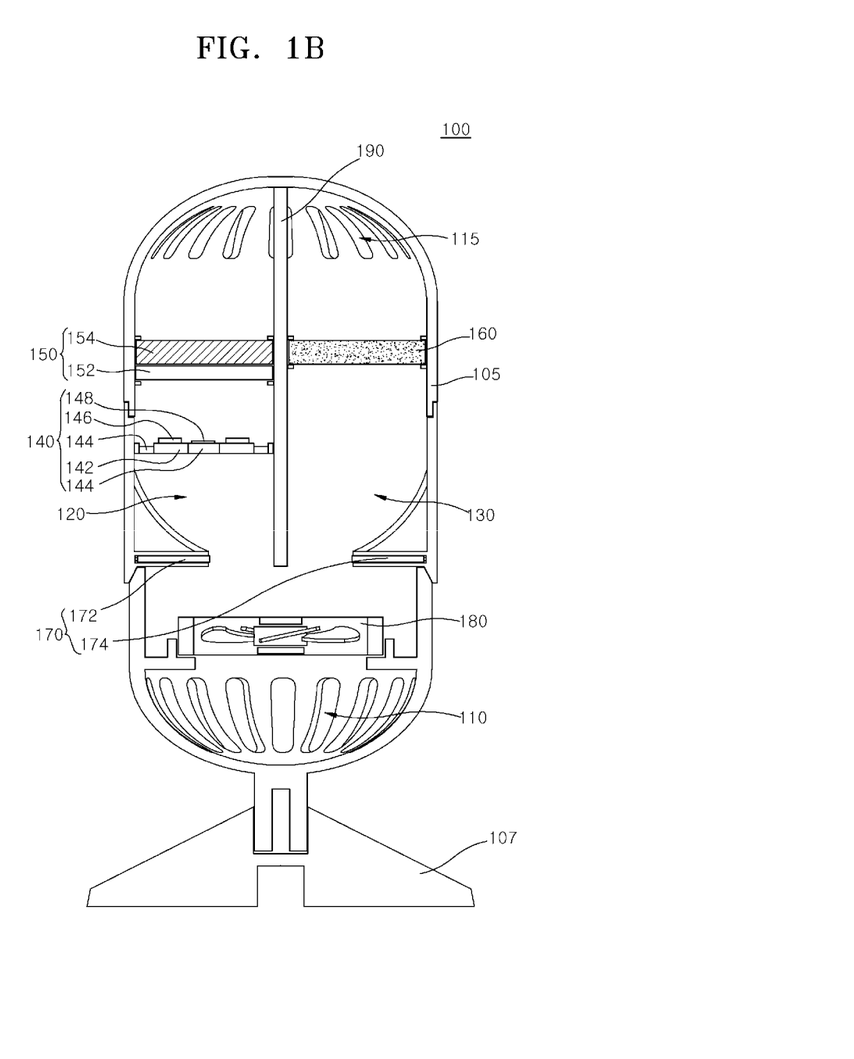
FIG. 1B is a cross-sectional view taken along line A-A' in the air purifying apparatus of FIG. 1A.

FIG. 1B is a cross-sectional view taken along line A-A' in the air purifying apparatus of FIG. 1A. For example, an air purifying apparatus, which is designated by reference numeral 100, may be an air cleaner for purifying indoor air.

Referring to FIGS. 1A and 1B, the air purifying apparatus 100 may include a body 105 defining a frame. As shown in the drawing, the body 105 may be supported by a support structure 107.

The body 105 includes a first conduit 120 and a second conduit 130 through which air flows from air inlets 110 to air outlets 115. The first and second conduits 120 and 130 may be arranged in the body 105 so as to be compatible with each other.

An air circulation device 180 may be disposed adjacent to the air inlets 110. The air circulation device 180 may be, for example, a blower fan. The air circulation device 180 may be, for example, a fan that upwardly moves air introduced into the air inlets 110.

The first and second conduits 120 and 130 may be disposed above the air circulation device 180 and may serve as passages through which air flowing through the air circulation device 180 moves upward. The first and second conduits 120 and 130 may be physically separated from each other by a partition wall portion 190. Air moving to one of the first and second conduits 120 and 130 may not be mixed with air moving to the other conduit until it is discharged from the body 105 through the air outlets 115. Alternatively, although not shown in the drawings, air passing through a first filter part 150 and air passing through a second filter part 160 may instead be discharged through the air outlets 115 in a mixed state.

An opening and closing device 170 may be disposed across entrances of the first and second conduits 120 and 130 adjacent to the air circulation device 180. The opening and closing device 170 may include a first opening and closing portion 172 acting on the first conduit 120 and a second opening and closing portion 174 acting on the second conduit 130. The first and second opening and closing portions 172 and 174 may respectively open and close the first and second conduits 120 and 130. Thus, the opening and closing device 170 may control the passage of air such that air passing through the air circulation device 180 may pass through at least one of the first and second conduits 120 and 130. That is, for example, when both of the first and second opening and closing portions 172 and 174 are opened, air may branch to the first and second conduits 120 and 130 and then flow upward. On the contrary, when one of the first and second opening and closing portions 172 and 174 is opened and the other is closed, air may flow upward through opened one of the first and second conduits 120 and 130.

Referring to the drawings again, an ultraviolet light emitting diode part 140 and a first filter part 150 may be disposed within the first conduit 120. The ultraviolet light emitting diode part 140 may include light emitting diodes for sterilization 146 and light emitting diodes for photocatalyst 148. The light emitting diodes for sterilization 146 and the light emitting diodes for photocatalyst 148 may be disposed on a support member 142 having openings 144. The first filter part 150 may include a photocatalytic filter 152 and a collection filter 154. In the first filter part 150, the photocatalytic filter 152 and the collection filter 154 may be arranged in order adjacent to the ultraviolet light emitting diode part 140.

The ultraviolet light emitting diode part 140 purifies air flowing in the first conduit 120 in conjunction with the first filter part 150. Each of the light emitting diodes for sterilization 146 may emit, for example, ultraviolet light of about 200 to 400 nm. Specifically, each of the light emitting diodes for sterilization 146 may emit ultraviolet light of about 200 to 290 nm. The light emitting diodes for sterilization 146 may perform a sterilization function for removal of bacteria in air flowing in the first conduit 120, using the ultraviolet light within the wavelength ranges listed above. In addition, the light emitting diodes for sterilization 146 may sterilize bacteria captured by the collection filter 154 by irradiating them with ultraviolet light having wavelengths within the ranges listed above.

Each of the light emitting diodes for photocatalyst 148 may emit, for example, ultraviolet light of about 200 to 400 nm. Specifically, for example, each of the light emitting diodes for photocatalyst 148 may emit ultraviolet light of about 320 to 400 nm. The emitted ultraviolet light reacts with the photocatalytic filter 152 to generate hydroxyl radicals such that the light emitting diodes for photocatalyst 148 may deodorize the air.

In an embodiment, the deodorization function using the light emitting diodes for photocatalyst 148 and the photocatalytic filter 152 or the sterilization function using the light emitting diodes for sterilization 146 may also be selectively performed. That is, one of the light emitting diodes for photocatalyst 148 and the light emitting diodes for sterilization 146 may be selectively operated. Thus, when one of the light emitting diodes 146 and 148 is operated, one of the associated deodorization and sterilization functions may be performed. In another embodiment, the deodorization function using the light emitting diodes for photocatalyst 148 and the photocatalytic filter 152 and the sterilization function using the light emitting diodes for sterilization 146 may also be simultaneously performed. That is, when both of the light emitting diodes for photocatalyst 148 and the light emitting diodes for sterilization 146 are operated, the deodorization and sterilization functions may be simultaneously performed. Air purified by the above-mentioned deodorization and/or sterilization functions may be discharged out of the body 105 through the air outlets 115.

Referring to the drawing again, the second filter part 160 may be disposed within the second conduit 130. The second filter part 160 may include a filter having a relatively smaller differential pressure applied between front and rear ends of the filter, compared to the first filter part 150. For example, the filter included in the second filter part 160 may have a smaller mesh than that of the filter included in the first filter part 150. That is, the number of holes per unit area in the filter included in the second filter part 160 is less than that in the filter included in the first filter part 150, thereby enabling the velocity of air passing through the filter of the second filter part 160 to be increased. Consequently, the differential pressure applied between the front and rear ends of the filter in the second filter part 160 may be reduced compared to the first filter part 150. On the other hand, the first filter part 150 may include a filter having a relatively larger differential pressure applied between front and rear ends of the filter, compared to the second filter part 160. In this case, the filter included in the first filter part 150 may have a larger mesh than that of the filter included in the second filter part 160.

In an embodiment, when the first filter part 150 includes the photocatalytic filter 152 and the collection filter 154, the second filter part 160 may include a carbon filter 160. The carbon filter 160 includes activated carbon and a catalyst so that organic chemical substances in air flowing in the second conduit 130 are filtered out through the carbon filter 160. Consequently, it may be possible to deodorize introduced air. In addition, if it is satisfied that the second filter part 160 has a smaller differential pressure compared to the first filter part 150, various functional filters may also be provided. As described above, air purified in the second conduit 130 may be discharged out of the body 105 through the air outlets 115.

As described above, the air purifying apparatus 100 of the present embodiment may deodorize and sterilize air flowing through the first conduit 120 and deodorize air flowing through the second conduit 130.

Figure 2A:
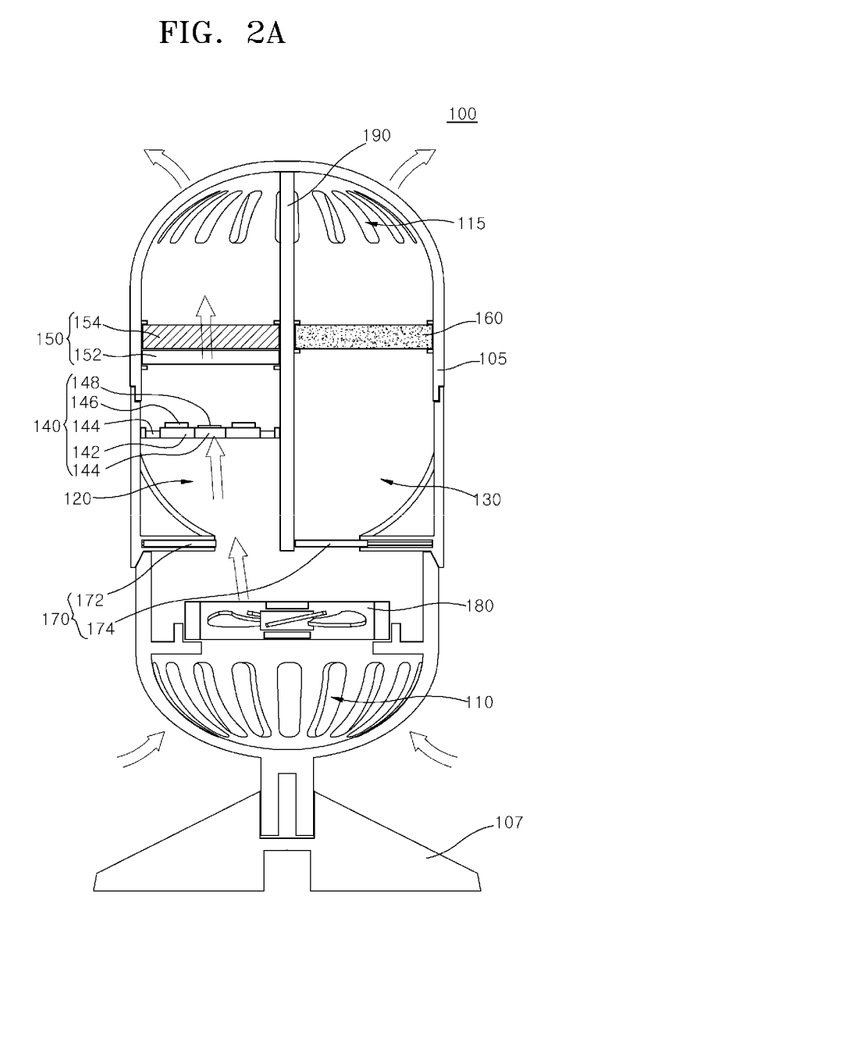
FIGS. 2A and 2B are schematic views that illustrate an operation of the air purifying apparatus according to an embodiment of the air purifying apparatus.
Figure 2B:
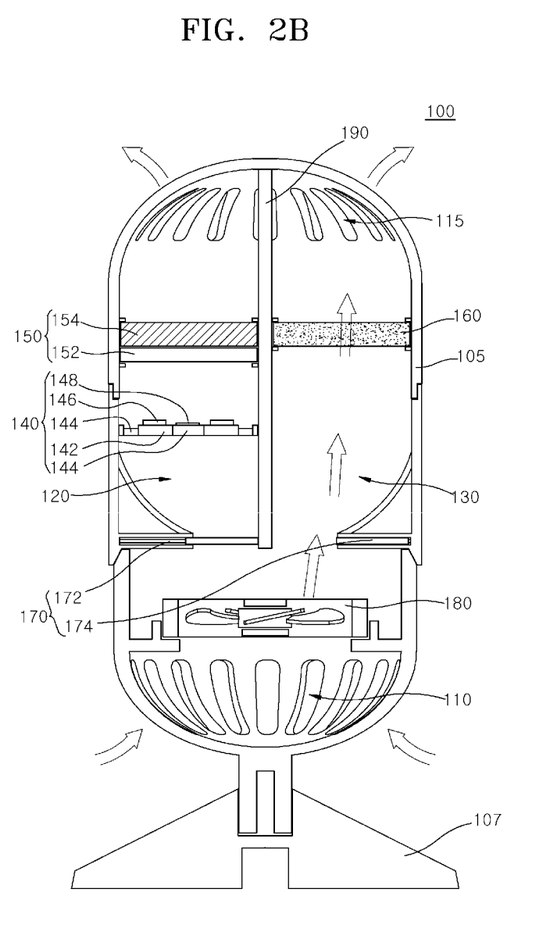

FIGS. 2A and 2B are views for schematically explaining an operation of the air purifying apparatus according to the embodiment of the present disclosure. FIG. 2A shows a state in which air introduced into the body 105 flows through the first conduit 120. As shown in the drawing, it may be possible to control the first and second opening and closing portions 172 and 174 such that the first opening and closing portion 172 is opened and the second opening and closing portion 174 is closed. In this case, air may flow only through the first conduit 120. The first conduit 120 may be provided therein with the ultraviolet light emitting diode part 140 and the first filter part 150, which may perform at least one of the deodorization and sterilization functions. When air is purified during flowing in the first conduit 120, at least one of the deodorization and sterilization functions may be performed. However, the volume and pressure of air discharged through the air outlets 115 may be decreased.

FIG. 2B shows a state in which air introduced into the body 105 flows through the second conduit 130. As shown in the drawing, it may be possible to control the first and second opening and closing portions 172 and 174 such that the first opening and closing portion 172 is closed and the second opening and closing portion 174 is opened. In this case, air may flow only through the second conduit 130. The second conduit 130 may be provided therein with the second filter part 160 which may perform the deodorization function. When air is purified during flowing in the second conduit 130, the deodorization function may be merely performed. However, the volume and pressure of air discharged through the air outlets 115 may be relatively increased.

As such, the present embodiment configures the air conduits such that an air passage may branch, so that air volume and air pressure at the air outlets may be selectively controlled. In the conventional air purifying apparatus, a method of increasing performance of the air circulation device 180 is adopted in order to increase air volume and air pressure at the air outlets. However, this method may cause an increase in cost of the air circulation device 180. In the present embodiment, since the air passage is selectively controlled by the opening and closing device 170 without an increase in output of the air circulation device 180, it may be possible to increase air volume and air pressure at the air outlets even when at least the deodorization function is performed.

Figure 3:
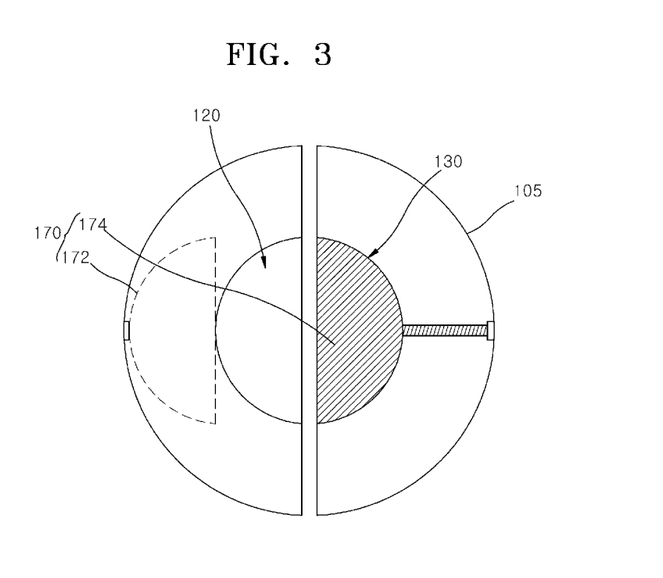
FIG. 3 is a cross-sectional view schematically illustrating an opening and closing device according to the embodiment of the air purifying apparatus.

FIG. 3 is a cross-sectional view schematically illustrating the opening and closing device according to an embodiment. The opening and closing device 170 may include the first opening and closing portion 172 and the second opening and closing portion 174 which selectively open and close the respective first and second conduits 120 and 130. The first and second opening and closing portions 172 and 174 may be separately controlled. As shown in the drawings, the first and second opening and closing portions 172 and 174 may be configured such that the first conduit 120 is opened and the second conduit 130 is closed by reciprocating motion. However, since the structure of the shown opening and closing device 170 is illustrated as an example, other modified examples having known configurations may also be applied to the opening and closing device 170.

Figure 4:
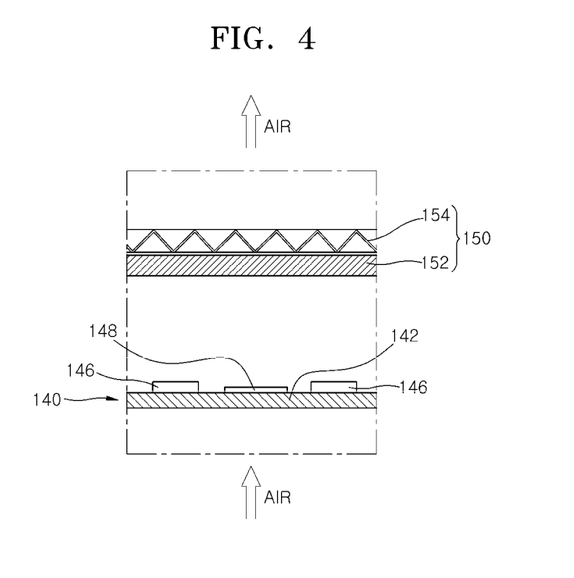
FIG. 4 is a cross-sectional view schematically illustrating an ultraviolet light emitting diode part and a first filter part according to the embodiment of the air purifying apparatus.

FIG. 4 is a cross-sectional view schematically illustrating the ultraviolet light emitting diode part and the first filter part according to the embodiment of the present disclosure. Referring to FIG. 4, in the ultraviolet light emitting diode part 140, the light emitting diodes for sterilization 146 and the light emitting diodes for photocatalyst 148 may be arranged on the support member 142 having openings (not shown) through which air flows. The light emitting diodes for sterilization 146 and the light emitting diodes for photocatalyst 148 may be disposed such that the direction of ultraviolet light emitted therefrom substantially coincides with the flow direction of air in the body 105.

The support member 142 may be made of a material having high thermal conductivity so as to conduct heat generated when the light emitting diodes for sterilization 146 and the light emitting diodes for photocatalyst 148 are operated. For example, the support member 142 may be made of metal.

The light emitting diodes for sterilization 146 may emit ultraviolet light for the removal of bacteria in air. Each of the light emitting diodes for sterilization 146 may emit, for example, ultraviolet light of about 200 to 400 nm. Specifically, each of the light emitting diodes for sterilization 146 may emit ultraviolet light of about 200 to 290 nm. The light emitting diodes for photocatalyst 148 may emit ultraviolet light for reacting with the photocatalytic filter 152. Each of the light emitting diodes for photocatalyst 148 may emit, for example, ultraviolet light of about 200 to 400 nm. Specifically, each of the light emitting diodes for photocatalyst 148 may emit ultraviolet light of about 320 to 400 nm.

In the present embodiment, the light emitting diodes are classified as light emitting diodes for photocatalyst and light emitting diodes for sterilization and are arranged according to functions of the light emitting diodes. However, in some embodiments, such classification may not be strictly appropriate. That is, in a region in which wavelength ranges of ultraviolet light generated by the light emitting diodes overlap, the light emitting diodes for photocatalyst may also perform a sterilization function and the light emitting diodes for sterilization may also generate a photocatalytic reaction together with the photocatalytic filter.

The first filter part 150 may include the photocatalytic filter 152 and the collection filter 154. The photocatalytic filter 152 may be a photocatalytic medium and include a substance providing a photocatalytic reaction. For example, the photocatalytic medium may include a titanium oxide ($TiO_2$), a silicon oxide ($SiO_2$), a tungsten oxide ($WO_3$), or a zirconium oxide (ZnO). The photocatalytic filter 152 may be formed in a layered structure including a titanium oxide ($TiO_2$). The photocatalytic filter 152 may be manufactured by a layer coated with a material such as metal foam or porous metal through which air may flow.

The photocatalytic filter 152 may promote a photocatalytic reaction when ultraviolet light is emitted from the light emitting diodes for photocatalyst 148. When the ultraviolet light is absorbed into the photocatalytic medium, electrons (e−) and holes (+) may be generated on a surface of the photocatalytic medium and, as such, the electrons may react with oxygen on the surface of the photocatalytic medium to generate superoxide anions ($O_2^-$). In addition, the holes may react with moisture present in air to generate hydroxyl radicals ($OH^-$). In this case, the generated hydroxyl radicals may oxidize and decompose organic substances. Consequently, containments and odor substances in air introduced into the air purifying apparatus may be decomposed and converted into water and carbon dioxide. In this way, the photocatalytic filter 152 may deodorize introduced air by cooperating with the light emitting diodes for photocatalyst 148.

The collection filter 154 performs a function of capturing bacteria in introduced air. To this end, the collection filter 154 may have fine pores such that bacteria do not easily pass through the collection filter 154. In order to increase a surface area of the collection filter 154 to increase a captured amount per unit area, the collection filter 154 may include a filter substance having a folded shape in the flow direction of air as shown in the drawing. Bacteria captured by the collection filter 154 may be sterilized by ultraviolet light emitted from the light emitting diodes for sterilization 146. The collection filter 154 may increase a time for which bacteria in air are exposed to ultraviolet light for sterilization, thereby enhancing sterilization efficiency of the light emitting diodes for sterilization 146. The collection filter 154 may be, for example, a known cabin filter. In some embodiments, the collection filter 154 may include germicides. Sterilization efficiency may be further enhanced by the germicides.

Figure 5:
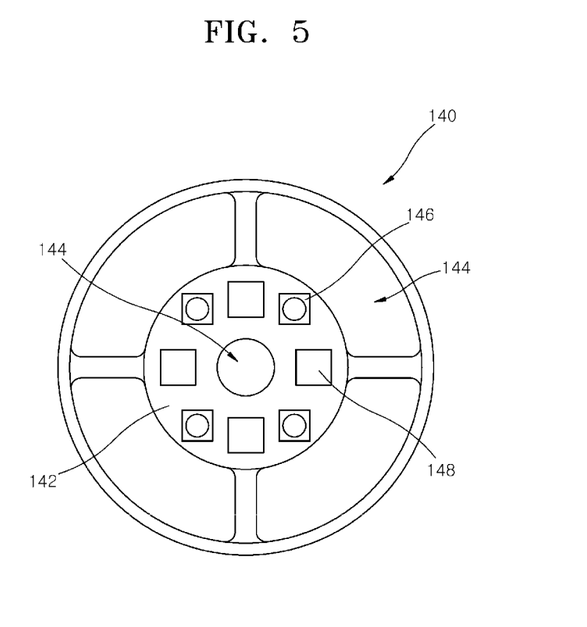
FIG. 5 is a view schematically illustrating the ultraviolet light emitting diode part according to an embodiment of the air purifying apparatus.

FIG. 5 is a view schematically illustrating the ultraviolet light emitting diode part according to an embodiment. Referring to FIG. 5, the ultraviolet light emitting diode part 140 may include a support member 142 on which the light emitting diodes for sterilization 146 and the light emitting diodes for photocatalyst 148 are mounted. The support member 142 may include the openings 144 provided at an outside portion and at a central portion thereof such that air flows through the openings 144. The support member 142 may be made of a material such as metal having high thermal conductivity.

As shown in the drawing, since the light emitting diodes for sterilization 146 and the light emitting diodes for photocatalyst 148 may be alternately arranged on the support member 142, ultraviolet light may be uniformly irradiated toward the first filter part 150.

The ultraviolet light emitting diode part 140 is not limited necessarily to the shown configuration. For example, the ultraviolet light emitting diode part 140 may be arranged in various configurations. That is, if the openings 144 are located such that air may smoothly flow through the openings 144, the openings 144 may be formed at various positions of the support member 142. The light emitting diodes for sterilization 146 and the light emitting diodes for photocatalyst 148 may be arranged in various modified configurations. For example, the light emitting diodes for sterilization 146 and the light emitting diodes for photocatalyst 148 may be arranged in a partitioned manner such that a plurality of light emitting diodes for sterilization 146 is present in one region and a plurality of light emitting diodes for photocatalyst 148 is present in the other region.

As described above, in accordance with the embodiments of the present disclosure, the air purifying apparatus may include the air conduits allowing the air passage to branch. An operation at a low air volume mode for performing sterilization and deodorization functions or an operation at a high air volume mode for performing a sterilization function may be selectively determined. In the related art, a method of increasing output of an air circulation device such as a circulation fan is adopted in order to increase air volume and air pressure at an air outlet. On the contrary, in the present embodiments, it may be possible to perform an air purification function at the high air volume mode, in addition to a method of increasing output of the air circulation device. Although the present embodiment illustratively describes a case in which the deodorization function is possible during the operation at the high air volume mode, the present disclosure is not limited thereto. If it is satisfied that a differential pressure between the front and rear ends of the second filter part is less than that between the front and rear ends of the first filter part, the second filter part may include various functional filters. In this case, the second filter part may include a filter which may perform the sterilization function. Consequently, the second filter part may perform the sterilization and deodorization functions.

In addition, in the present embodiment, the air purifying apparatus may be operated in a state in which the first conduit 120 is opened together with the second conduit 130. In this case, it may be possible to simultaneously and efficiently perform sterilization and deodorization functions and to properly adjust air volume and air pressure, compared to a case in which the first or second conduit 120 or 130 is selectively opened.

As is apparent from the above description, according to embodiments of the present disclosure, it may be possible to configure different air conduits such that an air passage may branch differently to arrange filters having different differential pressures across their respective conduits. Consequently, air volume and air pressure at an air outlet may be selectively controlled.

In accordance with embodiments of an air purifying apparatus as disclosed herein, an operation at a low air volume mode for performing sterilization and deodorization functions or an operation at a high air volume mode for performing a sterilization function may be selectively performed without the aid of a blower fan.

The embodiments of the present air purifying apparatus have been disclosed above for illustrative purposes. Those skilled in the art will appreciate that various modifications, additions, and substitutions are possible, without departing from the scope and spirit of the inventive concept as disclosed in the accompanying claims, and their equivalents.

Further, in describing embodiments, the specification may have presented methods and/or processes as particular sequences of steps. However, to the extent that the methods or processes do not rely on the particular order of steps set forth herein, the methods or processes should not be limited to the particular sequences of steps described. As one of ordinary skill in the art would appreciate, other sequences of steps may be possible. Therefore, the particular order of the steps set forth in the specification should not be construed as limitations on the claims. In addition, the claims directed to the methods and/or processes should not be limited to the performance of their steps in the order written, and one skilled in the art can readily appreciate that the sequences may be varied.

What is claimed is:

1. An air purifying apparatus comprising:
   a body having an inlet chamber and an outlet chamber, said body having first and second conduits through which air flows from air inlets to air outlets;
   an ultraviolet light emitting diode part and a first filter part disposed within the first conduit; and
   a second filter part disposed within the second conduit;
   wherein the inlet chamber comprises a series of inlet slots functioning as the air inlets and the outlet chamber comprises a series of outlet slots functioning as the air outlets; and
   an axial fan blowing air axially from the inlet slots towards both the first conduit and the second conduit;
   wherein the first conduit comprises a first opening and closing device and the second conduit comprises a second opening and closing device;
   wherein the outlet chamber comprises a fixed partition wall keeping air flowing through the first conduit completely separate from air flowing through the second conduit such that air flowing through the first conduit and air flowing through the second conduit do not mix until the air is discharged from the outlet slots; and
   wherein when the first opening and closing device and the second opening and closing device are both open, air flowing through the first conduit mixes with air flowing through the second conduit after the air is discharged through the outlet slots.

2. The air purifying apparatus of claim 1, wherein a filter included in the filter part has a relatively larger differential pressure between front and rear ends of the filter, compared to a filter included in the second filter part.

3. The air purifying apparatus of claim 2, wherein the filter included in the first filter part has a larger mesh than the filter included in the second filter part.

4. The air purifying apparatus of claim 2, wherein:
   the first filter part comprises a photocatalytic filter and a collection filter; and
   the second filter part comprises a carbon filter.

5. The air purifying apparatus of claim 1, wherein the ultraviolet light emitting diode part comprises:
   a light emitting diode for photocatalyst configured to act with a photocatalytic filter; and
   a light emitting diode for sterilization configured to remove bacteria,
   wherein the light emitting diode for photocatalyst and the light emitting diode for sterilization are arranged on a support member made of a material that has a high thermal conductivity.

6. The air purifying apparatus of claim 5, wherein the support member has an opening through which air is capable of flowing.

7. The air purifying apparatus of claim 1, wherein the outlet chamber has a domed outlet portion, and wherein the air outlet slots are disposed circumferentially around the domed outlet portion of the outlet chamber.

8. The air purifying apparatus of claim 1, wherein when the first opening and closing device and the second opening and closing device are open, air branches to the first conduit towards the first filter part and to the second conduit towards the second filter part.

9. An air purifying apparatus comprising:
   a body having an inlet chamber and an outlet chamber, said body having air inlets and air outlets;
   an axial fan blowing air axially from the air inlets to the air outlets;
   a first conduit and a second conduit allowing the flow of air to branch within the body; and
   a first filter part disposed within the first conduit and a second filter part disposed within the second conduit;
   wherein the first conduit comprises a first opening and closing device and the second conduit comprises a second opening and closing device;
   wherein the inlet chamber comprises a series of inlet slots functioning as the air inlets and the outlet chamber comprises a series of outlet slots functioning as the air outlets;
   wherein the outlet chamber comprises a fixed partition wall keeping air flowing through the first conduit completely separate from air flowing through the second conduit when the first opening and closing device and the second opening and closing device are both open such that air flowing through the first conduit and air flowing through the second conduit do not mix until the air is discharged from the outlet slots, and
   wherein when the first opening and closing device and the second opening and closing device are both open, air flowing through the first conduit mixes with air flowing through the second conduit after the air is discharged through the outlet slots.

10. The air purifying apparatus of claim 9, wherein a filter included in the filter part has a relatively larger differential pressure between front and rear ends of the filter, compared to a filter included in the second filter part.

11. The air purifying apparatus of claim 10, wherein the filter included in the first filter part has a larger mesh than the filter included in the second filter part.

12. The air purifying apparatus of claim 9, wherein when the first opening and closing device and the second opening and closing device are open, air branches towards the first filter part and towards the second filter part.

13. The air purifying apparatus of claim 9, wherein the light emitting diode for photocatalyst emits ultraviolet light of 320 to 400 nm and the light emitting diode for sterilization emits ultraviolet light of 200 to 290 nm.

14. An air purifying apparatus comprising:
   a body having an inlet chamber and an outlet chamber, said inlet chamber including a series of inlet slots and said outlet chamber including a series of outlets slots;
   an axial fan disposed adjacent to the inlet slots blowing air axially towards a first conduit and a second conduit;
   a first filter part disposed within the first conduit and a second filter part disposed within the second conduit;
   an ultraviolet light emitting diode part disposed adjacent to the first filter within the first conduit;
   wherein the outlet chamber comprises a fixed partition wall keeping air flowing through the first conduit completely separate from air flowing through the second conduit such that air flowing through the first conduit and air flowing through the second conduit do not mix until the air is discharged from the outlet slots, and
   wherein the air flowing through the first conduit mixes with the air flowing through the second conduit after the air is discharged through the outlet slots,
   wherein the ultraviolet light emitting diode part comprises:
   at least two light emitting diodes for photocatalyst configured to act with a photocatalytic filter; and
   at least two light emitting diodes for sterilization configured to remove bacteria, wherein the light emitting diodes for photocatalyst and the light emitting diodes for sterilization are alternately arranged on a support member made of a material that has a high thermal conductivity, wherein the support member defines outer openings at an outside portion of the support member and a central opening at a center of the support member.

15. The air purifying apparatus of claim 14, wherein the light emitting diode for photocatalyst emits ultraviolet light of 320 to 400 nm and the light emitting diode for sterilization emits ultraviolet light of 200 to 290 nm.

16. The air purifying apparatus of claim 14, wherein:
the first filter part comprises a photocatalytic filter and a collection filter; and
the second filter part comprises a carbon filter.

17. The air purifying apparatus of claim 16, wherein the ultraviolet light emitting diode part, the photocatalytic filter, and the collection filter are sequentially arranged along the flow of air in the first conduit.

18. The air purifying apparatus of claim 17, wherein:
the photocatalytic filter reacts with ultraviolet light emitted from the ultraviolet light emitting diode part so as to perform a deodorization function; and
the collection filter captures bacteria in air flowing in the first conduit and receives ultraviolet light emitted from the ultraviolet light emitting diode part so as to perform a sterilization function.

19. The air purifying apparatus of claim 14, wherein the first filter part has a relatively larger differential pressure between front and rear ends of the first filter part, compared to a differential pressure between front and rear ends of the second filter part.

20. The air purifying apparatus of claim 14, wherein the first filter part comprises a filter that has a larger mesh than a filter in the second filter part.

* * * * *